US008721963B2

(12) United States Patent
Matthews et al.

(10) Patent No.: US 8,721,963 B2
(45) Date of Patent: May 13, 2014

(54) COLD STERILIZATION OF TISSUE ENGINEERING SCAFFOLDS WITH COMPRESSED CARBON DIOXIDE

(75) Inventors: Michael A. Matthews, Columbia, SC (US); Jian Zhang, Sunnyvale, CA (US); Aidaris Jimenez, Hamilton, OH (US)

(73) Assignee: University of South Carolina, Columbia, SC (US)

( * ) Notice: Subject to any disclaimer, the term of this patent is extended or adjusted under 35 U.S.C. 154(b) by 328 days.

(21) Appl. No.: 13/074,220

(22) Filed: Mar. 29, 2011

(65) Prior Publication Data
US 2011/0236256 A1 Sep. 29, 2011

Related U.S. Application Data

(60) Provisional application No. 61/341,272, filed on Mar. 29, 2010.

(51) Int. Cl.
| *A61L 2/00* | (2006.01) |
| *B08B 7/00* | (2006.01) |
| *B08B 9/093* | (2006.01) |
| *A01N 1/02* | (2006.01) |
| *A61K 8/22* | (2006.01) |
| *A61L 2/20* | (2006.01) |
| *A61K 31/337* | (2006.01) |
| *A61K 31/70* | (2006.01) |
| *A61K 31/7088* | (2006.01) |
| *A61K 45/06* | (2006.01) |

(52) U.S. Cl.
CPC ............. *A01N 1/0215* (2013.01); *A61K 8/22* (2013.01); *A61L 2/00* (2013.01); *A61L 2/208* (2013.01); *A61K 2300/00* (2013.01); *A61K 31/337* (2013.01); *A61K 31/70* (2013.01); *A61K 31/7088* (2013.01); *A61K 45/06* (2013.01)
USPC ......... 422/33; 422/1; 422/28; 134/6; 134/22.18

(58) Field of Classification Search
CPC ... A01N 1/0215; A61K 8/22; A61K 2300/00; A61K 31/337; A61K 31/70; A61K 31/7088; A61K 45/06; A61L 2/00; A61L 2/208
USPC ................... 422/1, 28, 33, 295; 134/6, 22.18; 424/426, 484, 93.7, 422; 514/262.1
See application file for complete search history.

(56) References Cited

U.S. PATENT DOCUMENTS

| 6,235,701 B1 | 5/2001 | Senger Elsbernd |
| 6,491,231 B1 | 12/2002 | Eliasson et al. |

(Continued)

FOREIGN PATENT DOCUMENTS

WO WO 03090805 11/2003

OTHER PUBLICATIONS

An et al., "Effects of sterilization on implant mechanical property and biocompatibility—A concise review". International Journal of Artificial Organs 2005, 28, 1126-1137.

(Continued)

*Primary Examiner* — Monzer R Chorbaji
(74) *Attorney, Agent, or Firm* — Dority & Manning, P.A.

(57) ABSTRACT

Methods for sterilizing a biocompatible hydrogel polymer are provided via treating the biocompatible hydrogel polymer with a supercritical $CO_2$ treatment composition at a treatment pressure of about 4 MPa to about 30 MPa and a treatment temperature of about 5° C. to about 75° C. The supercritical $CO_2$ treatment composition can be substantially pure $CO_2$ or may further include hydrogen peroxide (e.g., in an amount of about 10 ppm to about 1,000 ppm). In certain embodiments, the biocompatible hydrogel polymer can be treated with the supercritical $CO_2$ treatment composition for about 30 minutes to about 5 hours. According to these methods, treating the biocompatible hydrogel polymer can kill about 90% or more of any *S. aureus* and *E. coli* present in the biocompatible hydrogel polymer.

14 Claims, 7 Drawing Sheets

(56) References Cited

U.S. PATENT DOCUMENTS

| | | | |
|---|---|---|---|
| 6,966,144 B2 | 11/2005 | Eliasson et al. | |
| 7,293,570 B2 | 11/2007 | Jackson | |
| 2004/0033269 A1 | 2/2004 | Hei et al. | |
| 2005/0054702 A1 | 3/2005 | Dunn et al. | |
| 2005/0156065 A1 | 7/2005 | Eliasson | |
| 2005/0227897 A1 | 10/2005 | Nelson et al. | |
| 2009/0017091 A1* | 1/2009 | Daniloff et al. | 424/423 |
| 2009/0220605 A1* | 9/2009 | Wei et al. | 424/486 |

OTHER PUBLICATIONS

Ballestra et al., "Inactivation of *Escherichia coli* by carbon dioxide under pressure". Journal of Food Science 1996, 61, 829-831, 836.

Ballestra et al., "Influence of pressurized carbon dioxide on the thermal inactivation of bacterial and fungal spores". Lebensmittel-Wissenschaft und—Technologie 1998, 31, 84-88.

Bell et al. "Biomedical membranes from hydrogels and interpolymer complexes". Advances in Polymer Science 1995, 122, 125-175.

Cappuccino et al. Microbiology A Laboratory Manual 2001, 123.

Collier et al. "Comparison of cross-linked polyethylene materials for orthopaedic applications". Clinical orthopaedics and related research 2003, 414, 289-304.

Costa et al. "Invivo UHMWPE biodegradation of retrieved prosthesis". Biomaterials 1998, 19, 1371-1385.

Debs-Louka et al. "Effect of compressed carbon dioxide on microbial cell viability". Applied and Environmental Microbiology 1999, 65, 626-631.

Dillow et al. "Bacterial inactivation by using near- and supercritical carbon dioxide". Proceedings of the National Academy of Sciences of the United States of America 1999, 96, 10344-10348.

Elvassore et al. "Micro-organisms inactivation by supercritical CO2 in a semi-continuous process". In: Perrut M, Reverchon E, editors; Dec. 6-8, 2000; Antibes (France). p. 773-778.

Enomoto et al. "Inactivation of food microorganisms by high-pressure carbon dioxide treatment with or without explosive decompression". Bioscience Biotechnology and Biochemistry 1997, 61, 1133-1137.

Erkmen, O. "Antimicrobial effect of pressurized carbon dioxide on *Staphylococcus aureus* in broth and milk". Food Science & Technology (London) 1997, 30, 826-829.

Erkmen, O. "Effect of carbon dioxide pressure on *Listeria monocytogenes* in physiological saline and foods". Food Microbiology 2000, 17, 589-596.

Erkmen, O. "Inactivation of *Salmonella typhimurium* by high pressure carbon dioxide". Food Microbiology 2000, 17, 225-232.

Erkmen, O. "Effects of high-pressure carbon dioxide on *Escherichia coli* in nutrient broth and milk". International Journal of Food Microbiology 2001, 65, 131-135.

Erkmen, O. "Kinetic analysis of *Listeria monocytogenes* inactivation by high pressure carbon dioxide". Journal of Food Engineering 2001, 42, 7-10.

Farewell et al. "Effect of temperature on in vivo protein synthetic capacity in *Escherichia coli*". Journal of Bacteriology 1998, 180, 4704-4710.

Galas et al. "Humidity-conditioned gravimetric method to measure the water content of hydrogel contact lens materials". Optometry and Vision Science: Official Publication of the American Academy of Optometry 1993, 70, 577-586.

Ghandehari et al. "In vitro degradation of pH-sensitive hydrogels containing aromatic azo bonds". Biomaterials 1997, 18, 861-872.

Hong et al. "Non-thermal inactivation of *Lactobacillus plantarum* as influenced by pressure and temperature of pressurized carbon dioxide". International Journal of Food Science and Technology 1999, 34, 125-130.

Ishikawa et al. "Inactivation of *Bacillus* spores by the supercritical carbon dioxide micro-bubble method". Bioscience, Biotechnology, and Biochemistry 1997, 61, 1022-1023.

Jimenez et al. Evaluation of CO2-Based Cold Sterilization of a Model Hydrogel. Biotech Bioeng., 101(6), 1344-1352, 2008.

Kamihira et al. "Sterilization of microorganisms with supercritical carbon dioxide". Agricultural and Biological Chemistry 1987, 51, 407-12.

Kishida et al. "Hydrogels for biomedical and pharmaceutical applications". Polymeric Biomaterials (2nd Edition) 2002, 133-145.

Koros et al. "High-pressure sorption of carbon dioxide in solvent-cast poly(methyl methacrylate) and poly(ethyl methacrylate) films". Journal of Applied Polymer Science 1981, 26, 159-170.

Lee et al. "Synthesis and characteristics of interpenetrating polymer network hydrogel composed of chitosan and poly(acrylic acid)". Journal of Applied Polymer Science 1999, 73, 113-120.

Lopatin et al. "Structure and relaxation properties of medical-purposed polyacrylamide gels". Journal of Applied Polymer Science 2005, 96, 1043-1058.

McHugh et al. "Supercritical Fluid Extraction". Newton, MA: Butterworth-Heinemann. 1994, 1-16 p.

Park GB. "Burn wound coverings—a review". Biomaterials, Medical Devices, and Artificial Organs 1978, 6, 1-35.

Ruel-Gariepy et al. "Thermosensitive chitosan-based hydrogel containing liposomes for the delivery of hydrophilic molecules". Journal of Controlled Release 2002, 82, 373-383.

Sawan et al. "Evaluation of the Interactions Between Supercritical Carbon Dioxide and Polymeric Materials". Lowell, MA: Los Alamos National Laboratory. 1995, 7-32 p.

Schmidt et al. "Disinfection of textile materials contaminated with *E. coli* in liquid carbon dioxide". Journal of Cleaner Production 2005, 13, 881.

Span et al. "A new equation of state for carbon dioxide covering the fluid region from the triple-point temperature to 1100 K at pressures up to 800 MPa". Journal of Physical and Chemical Reference Data 1996, 25, 1509-1596.

Spilimbergo et al. "Non-thermal bacterial inactivation with dense CO2". Biotechnology and Bioengineering 2003, 84, 627-638.

Stockar, U. "Effect of a near-critical and supercritical fluid on the viability ratio of microbial cells". Progress in Biotechnology 1992, 8, 407-416.

White et al. "Effective terminal sterilization using supercritical carbon dioxide". Journal of Biotechnology 2006, 123, 504-515.

Wu et al. "Influence of the COOH and COONa groups and crosslink density of poly(acrylic acid)/montmorillonite superabsorbent composite on water absorbency". Polymer International 2001, 50, 1050-1053.

Zhang et al. "Synthesis and Properties of Sepiolite/poly(acrylic acid-co-acrylamide) Nanocomposites". Polymer Bulletin 2005, 55, 419-428.

Zhang et al. "On the mechanisms of deactivation of *Bacillus atrophaeus* spores using supercritical carbon dioxide". Journal of Supercritical Fluids 2006 38, 268-273.

Andrews et al. "Effects of sterilisation method on surface topography and in-vitro cell behaviour of electrostatically spun scaffolds." Biomaterials 2007, 28, 1014-1026.

Athanasiou et al. "Sterilization, toxicity, biocompatibility and clinical applications of polylactic acid/ polyglycolic acid copolymers." Biomaterials 1996, 17, 93-102.

Carrascosa et al. "Effect of gamma-sterilization process on PLGA microspheres loaded with insulin-like growth factor-I (IGF-I)." Journal of Biomaterials Applications 2003, 18, 95-108.

Desai et al. "Study of Gamma-Irradiation Effects on Chitosan Microparticles." Drug Delivery 2006, 13, 39-50.

Draganic et al. "Formation of primary yields of hydroxyl radical and hydrated electron in the gamma-radiolysis of water." J. Phys. Chem. 1973, 77, 765-772.

Fischbach et al. "Does UV irradiation affect polymer properties relevant to tissue engineering?" Surface Science 2001, 491, 333-345.

Gogolewski et al. "Sterility, mechanical properties, and molecular stability of polylactide internal-fixation devices treated with low-temperature plasmas." Journal of Biomedical Materials Research 1996, 32, 227-235.

Grimes et al. "The effect of choice of sterilisation method on the biocompatibility and biodegradability of SIS (small intestinal submucosa)." Bio-Medical Materials & Engineering 2005, 15, 65-71.

(56) References Cited

OTHER PUBLICATIONS

Hemmer et al. "Sterilization of Bacterial Spores by Using Supercritical Carbon Dioxide and Hydrogen Peroxide." Journal of Biomedical Material Research (Part B) 2007, 80, 511-518.
Holy et al. "Optimizing the sterilization of PLGA scaffolds for use in tissue engineering." Biomaterials 2001, 22, 25-31.
Huebsch et al. "Analysis of sterilization protocols for peptide-modified hydrogels." Journal of Biomedical Materials Research (Part B) 2005, 74, 440-447.
Kato et al. "Oxidative degradation of collagen and its model peptide by ultraviolet irradiation." J. Agric. Food Chem. 1992, 40, 373-379.
Kelly-Wintenberg et al. "Use of a one atmosphere uniform glow discharge plasma to kill a broad spectrum of microorganisms." Journal of Vacuum Science & Technology a—Vacuum Surfaces and Films 1999, 17, 1539-1544.
Lerouge et al. "Plasma Sterilization: A Review of Parameters, Mechanisms, and Limitations." Plasmas and Polymers 2001, 6, 175-188.
Majewski et al. "Effects of ultraviolet radiation on the type-I collagen protein triple helical structure: A method for measuring structural changes through optical activity." Physical Review E 2002, 65, 031920.
Markowicz et al. "The impact of vacuum freeze-drying on collagen sponges after gas plasma sterilization." Journal of Biomaterials Science 2006, 17, 61-75.
Moioli et al. "Sustained Release of TGFβ3 from PLGA Microspheres and Its Effect on Early Osteogenic Differentiation of Human Mesenchymal Stem Cells." Tissue Engineering 2006, 12, 537-546.
Nair. "Currently practised sterilization methods—some inadvertent consequences." Journal of Biomaterials Applications 1995 10, 121-135.
Noah et al. "Impact of sterilization on the porous design and cell behavior in collagen sponges prepared for tissue engineering." Biomaterials 2002, 23, 2855-2861.
O'Leary et al. "The toxicogenic potential of medical plastics sterilized with ethylene oxide vapors." Journal of Biomedical Materials Research 1968, 2, 297-311.
Ozalp et al. "Controlled release of vancomycin from biodegradable microcapsules." Journal of Microencapsulation 2001, 18, 89-110.
Rutala et al. "Comparative evaluation of the sporicidal activity of new low-temperature sterilization technologies: ethylene oxide, 2 plasma sterilization systems, and liquid peracetic acid." American Journal of Infection Control 1998, 26, 393-398.
Shearer et al. "Effects of Common Sterilization Methods on the Structure and Properties of Poly (D,L Lactic-Co-Glycolic Acid) Scaffolds." Tissue Engineering 2006, 12, 2717-2727.
Zhang et al. "Supercritical carbon dioxide and hydrogen peroxide cause mild changes in spore structures associated with high killing rate." Journal of Microbiological Methods 2007, 70, 442-451.
Casas et al. "Effect of addition of cosolvent on the supercritical fluid extraction of bioactive compounds from *Helianthus annuus* L." Journal of Supercritical Fluids 2007, 41, 43-49.
Charlton et al. "A comparison of the efficacy of lumen-cleaning devices for flexible gastrointestinal endoscopes." Australian Infection Control 2007, 12, 81-90.
Cholvin et al. "General compatibility". Handbook of biomaterials evaluation: Scientific, technical, and clinical testing of implant materials, 2nd edition, 1998, 507-522.
Ding et al. "A new era in pyrogen testing." Trends in Biotechnology 2001, 19, 277-281.
Donlan. "Biofilms and device-associated infections." Emerging Infectious Diseases 2001, 7, 277-281.
Fitzgerald. "Infections of hip prostheses and artificial joints." Infectious Disease Clinics of North America 1989, 3, 329-338.
Gagnon et al. "Endotoxin affinity for provisional restorative resins." Journal of Prosthodontics 1994, 3, 228-236.
Gorbet et al. "Endotoxin: The uninvited guest." Biomaterials 2005, 26, 6811-6817.
Granados et al. "Assessment of parameters associated to the risk of PVC catheter reuse." J Biomed Mater Res 2001, 58, 505-510.
Hagman. "Sterilization." Remington: The science and practice of pharmacy 2005, 776-801.
Heinrich et al. "Endotoxin in fine($PM_{2.5}$) and coarse ($PM_{2.5-10}$) particle mass of ambient aerosols: A temporal-spatial analysis." Atmospheric Environment 2003, 37, 3659-3667.
Joslyn. "Sterilization by heat". Disinfection, sterilization, and preservation, $3^{rd}$ edition, 1983, 27-30, 766-767.
King et al. "The mutual solubilities of water with supercritical and liquid carbon dioxide." Journal of Supercritical Fluids 1992, 5, 296-302.
Knoernschild et al. "Endotoxin adherence to and elution from two casting alloys." The International Journal of Prosthodontics 1994, 7, 22-29.
Kundsin et al. "Detection of Endotoxin on Sterile Catheters Used for Cardiac Catheterization." Journal of Clinical Microbiology 1980, 11, 209-212.
Liu et al. Formation of Water-in-$CO_2$ Microemulsions with Non-fluorous Surfactant Ls-54 and Solubilization of Biomacromolecules. Chem Eur J 2002, 8, 1356-1360.
Martich et al. "Response of man to endotoxin." Immunobiology 1993, 187, 403-416.
Morrison et al. "Current status of bacterial endotoxins." ASM News 1994, 60, 479-484.
Nakagawa et al. "Endotoxin contamination in wound dressings made of natural biomaterials." J Biomed Mater Res 2003, 66, 347-355.
Nelson et al. "Lipopolysacharide affinity for titanium implant biomaterials." The Journal of Prosthetic Dentistry 1997, 77, 76-82.
Novitsky et al. "Factors affecting recovery of endotoxin adsorbed to container surfaces." Journal of Parenteral Science and Technology 1986, 40, 284-286.
Ohno et al. "Lipopolysaccharide interaction with lysozyme: Binding of lipopolysaccharide to lysozyme and inhibition of lysozyme enzymatic activity." The Journal of Biological Chemistry 1989, 264, 4434-4441.
Pabst et al. "Bacterial LPS: A mediator of inflammation." Handbook of Inflammation 1989, 361-393.
Park et al. "Predictors of airborne endotoxin in the home." Environmental Health Perspectives 2001, 109, 859-864.
Raetz. "Biochemistry of endotoxins." Annual Review of Biochemistry 1990, 59, 129-170.
Ragab et al. "Measurement and removal of adherent endotoxin from titanium particles and implant surfaces." J Orthop Res 1999, 17, 803-809.
Ramakrishna. "Safety of technology: Infection control standards in endoscopy." Journal of Gastroenterology and Hepatology 2002, 17, 361-368.
Reyes et al. "Pyrogenic reactions after inadvertent infusion of endotoxin during cardiac catheterizations." Annals of Internal Medicine 1980, 93, 32-55.
Rietschel et al. "Bacterial endotoxins." Scientific American 1992, 267, 54-61.
Rietschel et al. "Bacterial endotoxin: molecular relationship of structure to function." The FASEB Journal 1994, 8, 217-225.
Rioufol et al. "Quantitative determination of endotoxins released by bacterial biofilms." Journal of Hospital Infection 1999, 43, 203-209.
Robinson et al. "*Porphyromonas gingivalis* endotoxin affinity for dental ceramics." Journal of Prosthetic Dentistry 1996, 75, 217-227.
Rudnick et al. "An outbreak of pyrogenic reactions in chronic hemodialysis patients associated with hemodialyzer reuse." Artif Organs 1995, 19, 289-294.
Rutala et al. Reprocessing endoscopes: United Stated perspective. Journal of Hospital Infection 2004, 56, 27-39.
Sweadner et al. "Filtration removal of endotoxin (pyrogens) in solution in different state of aggregation." Applied and Environment Microbiology 1977, 34, 382-385.
Tessarolo et al. "Efficiency in endotoxin removal by a reprocessing protocol for electrophysiology catheters based on hydrogen peroxide plasma sterilization." International Journal of Hygiene and Environmental Health 2006, 209, 557-565.
Tsuji et al. "Dry heat destruction of LPS: Drug heat destruction kinetics." Applied and Environment Microbiology 1978, 36, 710-714.

(56) References Cited

OTHER PUBLICATIONS

Weary et al. "A manufacturer's guide to depyrogenation." BioPharm Manuf 1988, 1, 22-29.

M. Belton, "Allergen impermeable covers appear clinically ineffective in the management of adult asthma patients." N Engl J. Med. 2003, 349, 3.

Bischoff et al., "Assessment of mite numbers: new methods and results." Experimental & Applied Acarology 1992, 16, 1-14.

de Boer et al., "The decay of house dust mite allergens, Der p I and Der p II, under natural conditions." Clin Exp Allergy 1995, 25, 765-770.

Eastoe et al., "Self-assembly in green solvents". Physical Chemistry Chemical Physics 2005, 7, 1352-1362.

Ginty et al., "Mammalian cell survival and processing in supercritical $CO_2$". Proceedings of the National Academy of Sciences 2006, 103, 7426-7431.

John et al., "Functional effects of the inhibition of the cysteine protease activity of the major house dust mite allergen der p 1 by a novel peptide-based inhibitor". Clinical and Experimental Allergy 200, 30, 784-793.

Jovanovic et al., "Stabilization of proteins in dry powder formulations using supercritical fluid technology". Pharmaceutical Research 2004, 21, 1955-69.

Kauffman et al., "House dust mite major allergens Der p 1 and Der p 5 activate human airway-derived epithelial cells by protease-dependent and protease-independent mechanisms." Clinical and Molecular Allergy 2006, 4:5.

Kawamoto et al., "Toward elucidating the full spectrum of mite allergens—state of the art." Journal of Bioscience and Bioengineering 2002, 94, 285-298.

Kort et al., "Four-year stability of Der p I in house dust under simulated domestic conditions in vitro." Allergy 1994, 49, 131-133.

Lau et al., "Placebo-controlled study of the mite allergen-reducing effect of tannic acid plus benzyl benzoate on carpets in homes of children with house dust mite sensitization and asthma." Pediatric Allergy and Immunology 2002, 13, 31-36.

Sidenius et al., "Decay of house-dust mite allergen Der f 1 at indoor climatic conditions." Annals of Allergy, Asthma & Immunology 2002, 89, 34-37.

Woodcock et al., "Control of Exposure to Mite Allergen and Allergen-Impermeable Bed Covers for Adults with Asthma." N Engl J Med 2003, 349, 225-236.

Zagrobelny et al., "In situ studies of protein conformation in supercritical fluids: Trypsin in carbon dioxide". Biotechnology Progress 1992, 8, 421-423.

Zhang et al., "Sterilizing *Bacillus pumilus* spores using supercritical carbon dioxide". Journal of Microbiological Methods 2006, 66, 479-485.
Zhang et al., "Sterilization using high-pressure carbon dioxide". Journal of Supercritical Fluids 2006, 38, 354-372.
U.S. Appl. No. 13/235,807, filed Sep. 19, 2011, Matthews et al., Methods and Compositions for Dislodging Debris Particles from a Substrate.
U.S. Appl. No. 13/070,845, filed Mar. 24, 2011, Matthews et al., Methods and Compositions for Eliminating Allergens and Allergen-Producing Organisms.
U.S. Appl. No. 13/197,261, filed Aug. 3, 2011, Matthews et al., Removal of Bacterial Endotoxins.

* cited by examiner

COLD STERILIZATION OF TISSUE ENGINEERING SCAFFOLDS WITH COMPRESSED CARBON DIOXIDE

PRIORITY INFORMATION

The present application claims priority to U.S. Provisional Patent No. 61/341,272 filed on Mar. 29, 2010 titled "Cold Sterilization of Tissue Engineering Scaffolds with Compressed Carbon Dioxide" of Matthews, et al., the disclosure of which is incorporated by reference herein.

GOVERNMENT SUPPORT CLAUSE

This invention was made with government support under R01EB55201 awarded by National Institutes of Health/National Institute of Bioengineering Research Partnership. The government has certain rights in the invention.

BACKGROUND

Rapid developments in surgical and implantable device technology pose challenges for current sterilization methods. This is particularly true for environment-sensitive biopolymers. The major sterilization methods used in hospitals include moist heat steam autoclaves, ethylene oxide gas, gamma irradiation and gas plasma. However, no single process is suitable for sterilizing all medical devices. Specifically for biopolymers, high temperatures (for thermally sensitive materials), toxic or oxidative chemical agents, and/or radiation may degrade performance and lower the biocompatibility of the biopolymers. Because of these limitations, the next generations of polymeric medical devices and heat sensitive biomaterials require new sterilization methods.

Terminal sterilization of manufactured products is a critical issue in the medical device and pharmaceutical industries. Because current sterilization methods pose significant drawbacks in specific biomedical applications, $SC-CO_2$ (supercritical-carbon dioxide) technology is a promising alternative. $SC-CO_2$ sterilization is a novel low temperature and biocompatible sterilization process. There is potential for using supercritical $CO_2$ technology in the emerging field of polymeric biomedical materials, encompassing both synthetic and natural polymers, and packaged materials. $CO_2$-based fluids have been tested for both inactivation and sterilization of organisms and compatibility with biomaterials, $CO_2$-based fluids with trace levels of additives are successful in killing organisms such as $B.$ $pumilus$ spores. Several medical grade polymers have been processed with $CO_2$ without degrading chemical and mechanical properties. By translating research into practice, $CO_2$ processing will be a suitable alternative for sterilizing thermally sensitive materials. $SC-CO_2$ has shown tremendous potential for the modification and processing of polymers, including common synthetic polymers.

The biocidal and sterilizing effects of high-pressure $CO_2$ mixtures have been quantified for various species of bacteria, and these results have recently been summarized. $CO_2$ technology is attractive in part because $CO_2$ is non-flammable, non-toxic, physiologically safe, chemically inert and readily available. When heated and compressed above its critical point (7.38 MPa and 304.2 K) $CO_2$ exhibits a liquid-like density (0.6-1.0×10−3 kg·m−3) but gas-like diffusivity (10−7-10−8 m2s−1) and viscosity (3-7×10−5 N·s·m−2). Because there is no vapor-liquid interface for pure $SC-CO_2$, there are no surface tension considerations. For two-phase mixtures (e.g. $CO_2$+water) near the $CO_2$ critical point, the surface tension is quite low. These properties allow $CO_2$ to penetrate porous structures easily. Typical $CO_2$ processing temperatures range up to 40° C., so there is the potential for developing a low-temperature sterilization technology. Research has shown that compressed $CO_2$ kills many clinically relevant gram-positive vegetative bacteria (e.g. *Listeria monocytogenes, Staphylococcus aureus*, and *Enterococcus faecalis*) and gram-negative vegetative bacteria (e.g. *Salmonella typhimurium, E. coli*, and *Pseudomonas aeruginosa*). Bacterial spores can also be sterilized with this process. A 6-log reduction of *B. pumilus, B. atrophaeus*, and *G. stearothermophilus* spores has been achieved at relatively low temperatures using $SC-CO_2$ (40° C., 27.58 MPa for 4 hours).

Significant attention has been focused on environment-responsive hydrogels because of their applications for stimuli-responsive drug delivery, in which they show changes in swelling behavior according to the external environment. The external aqueous environment affects the swelling and water content of any specific gel. These properties also depend on the ionic character of the gel, electrostatic forces, thermodynamic activity, and nature of the polymer. The presence of thermodynamically active functional groups on polymer chains makes these hydrogels sensitive to environmental factors. Incorporating acidic or basic groups render a hydrogel pH sensitive. The ability to control changes in the properties of a hydrogel leads to the potential for solving significant medical problems that cannot be addressed with conventional engineering plastics. Crosslinked poly(acrylic acid) and its copolymers, form a class of interesting hydrogels that can absorb, swell and retain aqueous solutions up to hundreds or thousands times their own weight, even under pressure.

As such, a need exists for a method of sterilizing a hydrogel polymer, particularly a biocompatible hydrogel polymer, from bacteria (e.g., *S. aureus* and *E. coli*).

SUMMARY

Objects and advantages of the invention will be set forth in part in the following description, or may be obvious from the description, or may be learned through practice of the invention.

Methods are generally provided for sterilizing a biocompatible hydrogel polymer via treating the biocompatible hydrogel polymer with a supercritical $CO_2$ treatment composition at a treatment pressure of about 4 MPa to about 30 MPa and a treatment temperature of about 5° C. to about 75° C. For example, the supercritical $CO_2$ treatment composition can be substantially pure $CO_2$ or may further include hydrogen peroxide (e.g., in an amount of about 10 ppm to about 1,000 ppm). In certain embodiments, the biocompatible hydrogel polymer can be treated with the supercritical $CO_2$ treatment composition for about 30 minutes to about 5 hours. According to these methods, treating the biocompatible hydrogel polymer can kill about 90% or more of any *S. aureus* and *E. coli* present in the biocompatible hydrogel polymer (e.g., about 95% or more, such as about 99% to 100%).

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1:
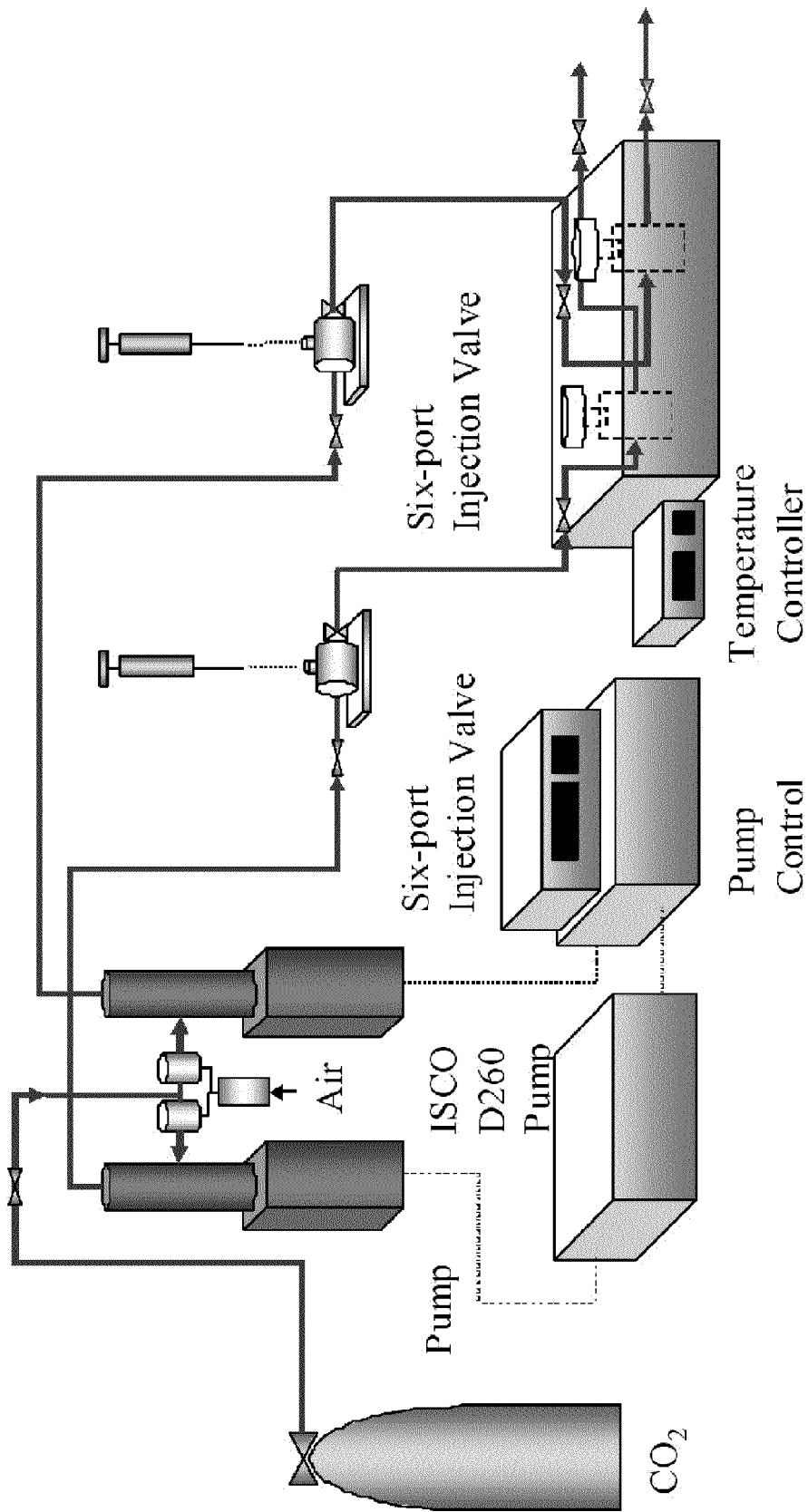
FIG. 1 shows a schematic of an exemplary high-pressure $CO_2$ apparatus.

The following description and other modifications and variations to the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention.

Methods are generally disclosed for sterilization of a biocompatible hydrogel polymer using $CO_2$-based technology. In one embodiment, the biocompatible hydrogel polymer can be sterilized using a $CO_2$-based cold sterilization process. In terms of both its killing efficiency and its effects on the physical properties of the hydrogel, a method is generally provided for sterilizing a biocompatible hydrogel polymer, these treatments can render significant killing and/or substantially complete killing efficiency of bacteria (e.g., *Staphylococcus aureus* and/or *Escherichia coli*) without significantly affecting the properties of the hydrogel polymer, such as its water content, swelling ratio, surface morphology, thermal stability, etc.

Biocompatible hydrogels are networks of polymer chains that are hydrophilic, sometimes found as a colloidal gel in which water is the dispersion medium. Hydrogels are highly absorbent (e.g., containing over 99% by weight water) natural or synthetic polymers. Hydrogels also possess a degree of flexibility very similar to natural tissue, due to their significant water content. A large number of synthetic hydrogels exist with potential for biomedical applications, and these vary by chemical structure, chemical functional groups, and molar mass. More recently, protein and peptide chains have been incorporated into the hydrogel network. Suitable biocompatible hydrogel polymers that can be sterilized include, but are not limited to, poly (acrylic acid-co-acrylamide) potassium salt; as well as hydrogels based on poly(vinyl alcohol); methyl cellulose; hyaluronan and derivatives; silicon hydrogels; and mixtures thereof. In one embodiment, the hydrogel polymer can form a hydrogel composition that contains at least water in an amount of about 50% by weight, such as about 75% by weight or more.

Hydrogels are a prime candidate for low temperature $CO_2$ sterilization because they are sensitive to high temperature and radiation. For instance, gamma irradiation is one of the most common sterilization techniques, even though it may cause unwanted polymer cross-linking. Also, gamma irradiation generates free radicals that may affect their clinical performance.

The unique behavior and flexibility of applications of hydrogels have led to a wide range of medical and pharmaceutical applications. Also, they can be tailored for excellent tissue compatibility, easy manipulation, and solute permeability. Hydrogels are excellent for controlled release applications over extended periods of time. Incorporation of a functional group in the matrix allows control of drug diffusion, responsiveness to the physiological environment, or recognition of a specific target. Hydrogels offer attractive opportunities for protein delivery, cancer therapy, topical delivery, wound dressing and nanogels. Hydrogels have also been extensively used in pure form or in the form of composites. Their swelling characteristics provide permeability, flexibility and occlusive properties.

The hydrogel polymer can be treated with a supercritical $CO_2$ (i.e., $SC-CO_2$) treatment composition at a treatment pressure and a treatment temperature. For example, in one embodiment, the supercritical $CO_2$ treatment composition can include substantially pure supercritical $CO_2$. Thus, in this embodiment, the supercritical $CO_2$ treatment composition can be substantially free of other components in the treatment composition. As used herein, the term "substantially free" means no more than an insignificant trace amount present and encompasses completely free (e.g., 0 molar % up to 0.0001 molar %). Alternatively, in other embodiments, the supercritical $CO_2$ treatment composition can include a combination of supercritical $CO_2$ and another antibacterial composition (e.g., hydrogen peroxide), which may be included in an amount of about 10 ppm to about 1,000 ppm, such as about 50 ppm to about 500 ppm, of the supercritical $CO_2$.

The treatment pressure and treatment temperature can be particularly selected to ensure maximum effectiveness of sterilization while not significantly altering the polymeric properties of the hydrogel. For example, the treatment pressure can be about 4 MPa to about 30 MPa. In certain embodiments, the treatment temperature can be about 5° C. to about 75° C., such as about 20° C. to about 50° C.

Treatment times can be as low as about 60 minutes. However, in most embodiments, the treatment time can be about 30 minutes to about 5 hours. For times less than 30 minutes, incomplete kill of the bacteria may not be achieved.

For example, treating the biocompatible hydrogel polymer can kill about 90% or more of any *S. aureus* and *E. coli* present in the biocompatible hydrogel polymer, such as about 95% or more or about 99% or more.

EXAMPLE

We illustrate one application of $CO_2$-based technology to sterilize a model hydrogel. The conditions used in this illustration are not intended to limit the application. The following example demonstrates the effectiveness of $CO_2$-based technology in killing *Staphylococcus aureus* (*S. aureus*) and *Escherichia coli* (*E. coli*) embedded in a model hydrogel (poly (acrylic acid-co-acrylamide) potassium salt). *S. aureus* and *E. coli* (Gram-positive and Gram-negative, respectively) were chosen based on their prevalence in medical contamination (e.g. nosocomial infections in hospitals). The $CO_2$ sterilization process has been proven for several microorganisms but not when the bacteria are embedded in a polymeric matrix. Furthermore, this example shows that the $CO_2$ sterilization process has no effect on several important physical properties of the hydrogel. Important physical properties of the hydrogel include water content and swelling ratio, evaluated before and after processing with $CO_2$. Also, the thermal stability was investigated by thermal gravimetric analysis (TGA) and the morphology of the surface by scanning electron microscopy (SEM).

Materials and Methods

Chemicals.

Poly (acrylic acid-co-acrylamide) potassium salt powder crosslinked (432776-250G, Batch #08902313) was obtained from Sigma-Aldrich. Difco™ tryptic soy agar (Becton, Dickinson and Company, Sparks, Md.), Bracto™ tryptic soy broth ((Becton, Dickinson and Company, Sparks, Md.) and 30% hydrogen peroxide ($H_2O_2$) aqueous solution were obtained from Fisher Scientific (Fair Lawn, N.J.). Anhydrous $CO_2$ (bone dry grade, purity>99.8%) used for the treatment of the polymer was obtained from National Specialty Gases (Durham, N.C.).

Bacteria.

*Staphylococcus aureus* (*S. aureus*) (ATCC 25923) and *Escherichia coli* (*E. coli*) (ATCC 15597) were used as test microorganisms embedded in the hydrogel to investigate the bacteriocidal activity of pure $SC-CO_2$ or $SC-CO_2+H_2O_2$.

Preparation of Bacteria Suspensions

Suspensions of *S. aureus* and *E. coli* were prepared for inoculation of the hydrogel. Cultures of these bacteria were preserved on Difco™ trypic soy agar and stored in Petri dishes inside of a refrigerator at 4° C. A fresh colony was transferred aseptically from the agar culture plate into a culture tube containing 30 g/L of sterile tryptone soy broth (TSB). The bacteria were grown to a logarithmic phase in the TSB at 35° C. for 24 hours (Cappuccino and Sherman 2001). A fresh bacterial culture was prepared before every experiment to ensure cell viability. Both *S. aureus* and *E. coli* bacteria suspensions were diluted after incubation to a concentration of approximately 107 colony forming units per milliliter (cfu/mL). A Petroff Hausser counting chamber was used to quantify the cfu count in the diluted samples. Also, a standard plate counting technique was followed to verify the original number of cfu. The final number of *S. aureus* or *E. coli* generally ranged from 7.6×106 to 2.3×108 cfu/mL. The hydrogel was hydrated with the diluted bacteria suspension of either *S. aureus* or *E. coli*.

Hydration and Inoculation of Dry Hydrogel Powders

For $CO_2$ sterilization experiments, the model gel was hydrated with the diluted bacteria suspension. Typically, 0.1 g of dry powder (absorption capacity of 200 mL $H_2O$/g) was hydrated with steam autoclaved DI water. The hydrated powder was left overnight inside of a refrigerator at 4° C. About 3 g of the completely incorporated hydrated gel were then transferred into a polyallomer centrifuge tube for the $CO_2$ treatment, to be described subsequently.

The effect of $CO_2$ processing on the swelling and water uptake of the hydrogel was also evaluated. The evaluation was made for hydrogel powders that were treated with either $CO_2$ or $CO_2$ plus $H_2O_2$. After treatment, the dry powders were hydrated as follows. A nylon filter and a 100 mm watch glass were weighed with a Sartorius balance (Brinkmann Instruments, Inc.). Hydrogel powders (approximately 0.25 grams) were soaked with 60 mL of deionized water for 24 hours in a graduated cylinder at approximately 4° C. (measured with a Traceable Thermometer from Fisher Scientific). After hydration, the gels were carefully blotted on a nylon filter, and excess water was removed through a Buchner funnel. The nylon filter with hydrated polymer was placed on the watch glass, and the hydrogels were vacuum dried at 50° C.

Processing with $CO_2$

Poly (acrylic acid-co-acrylamide) hydrogels (in dry powder, hydrated, or inoculated as per the specific experiment) were treated with $SC-CO_2$ using the $SC-CO_2$ treatment system shown in FIG. 1. The ISCO SFX 2-10 SC fluid extractor (Lincoln, Nebr.) has two 10 mL chambers in parallel. Prior to $SC-CO_2$ treatment, a steam autoclaved polyallomer centrifuge tube (Beckman Instruments, Inc., Calif.) containing the gel was transferred aseptically into the steam autoclaved, dry, 10 mL ISCO pressure cartridge. A pre-heater was used to heat the $CO_2$ (supplied from a standard cylinder) to 40° C. Before pressurizing, the vessel was flushed once with gaseous CO2 for about 10 s (~800 psi or 5.51 MPa). The inlet valve was opened while the vent valve was closed. Then, the inlet valve was closed and vent valve was slowly opened. Once heated, $CO_2$ was fed into the cartridge using an ISCO D260 syringe pump controlled by an ISCO series D controller; the process pressure was 27.6 MPa (4000 psi). In experiments where $H_2O_2$ was added as a sterilization aid, 5 μL of 30% $H_2O_2$ (equivalent to 200 ppm in 10 mL of $CO_2$) was transferred quantitatively into the $CO_2$ pressurized chamber through a Valco Instruments (Houston, Tex.) six-port liquid injection valve. The chamber remained at 40° C. for up to 4 hrs of treatment. $CO_2$ was slowly released through a 0.16 cm ($\frac{1}{16}$ inch) vent valve for approximately 30 minutes until the pressure returned to ambient. The chamber containing the hydrogel sample was immediately removed from the SFX 2-10 extractor and the contents were treated for the various assays described herein.

Quantification of Bacteria

A pulverization procedure was followed to quantify the amount of bacteria in the inoculated hydrogel. Bacteria were dislodged from the gel by pulverizing in a Stomacher 400 Circulator (Seward Ltd., United Kingdom) for 10 minutes at 230 revolutions per minute (rpm). The degree of killing was quantified with a standard plate counting technique. The log reduction of bacteria (*S. aureus* or *E. coli*) was calculated with equation (1), $$\text{Log reduction} = \log\left(\frac{\text{average number of bacteria on untreated hydrogel}}{\text{average number of bacteria on treated hydrogel}}\right) \quad (1)$$

For use as negative controls, a quantified amount of inoculated hydrogel (with either *S. aureus* or *E. coli*) in a polyallomer centrifuge tube was immersed in a PolyScience laboratory temperature bath (model 9105) at 40° C. for 4 hours. The inoculated hydrogel was removed from the bath, pulverized in the Stomacher 400, and the degree of killing was quantified using the standard plate counting technique.

Physical Characterization of Hydrogel Samples

The water content and swelling ratio of poly (acrylic acid-co-acrylamide) potassium salt hydrogel were evaluated. Dry hydrogel powders were hydrated and prepared to be vacuum dried at 50° C. in the vacuum oven. Each sample (hydrogel plus filter and watch glass) was periodically removed from the vacuum oven and weighed. The mass was recorded quickly to minimize evaporative losses to the atmosphere (if still saturated with water) or weight gain from the air (after a significant amount of water has been removed by the vacuum oven). Room temperature was about 21° C. The sample was returned to the vacuum oven immediately after weighing. Drying continued until the mass stabilized. The hydration and dehydration characteristics of the hydrogel are quantified by the drying curves and the swelling ratio.

The water gravimetric content or percent of water is defined and computed as follows (Galas and Enns 1993):

$$\% \text{ water content} = \frac{(\text{wet hydrogel weight} - \text{dry hydrogel weight})}{\text{wet hydrogel weight}} * 100 \quad (1)$$

Drying curves illustrate the percent of water content versus drying temperatures. Also, swelling characteristics of the hydrogel are given in terms of swelling ratio defined as (Dumitriu 2002):

$$\text{swelling ratio} = \frac{\text{weight of swollen gel}}{\text{weight of dry gel}} \quad (2)$$

The average equilibrium swelling ratios are given for the completely hydrated samples.

Hydrated samples were also analyzed by Thermogravimetric Analysis (TGA). A PerkinElmer TGA 7 Thermogravimetric Analyzer was used. TGA thermograms were carried out at a heating rate of 10° C./min under flowing helium (20 mL/min) from room temperature to 110° C. followed by a temperature hold at 110° C. for 30 min. The temperature program is controlled with Pyris™ software (CT, USA). The surface morphology of the hydrogel, before and after $CO_2$ processing, was examined by Scanning Electron Microscopy (SEM). Dried poly (acrylic acid-coacrylamide) potassium salt hydrogel powder was mounted onto an aluminum stud, and sputter-coated with conducting gold. SEM micrographs were taken with a JEOL 200CX Scanning Electron Microscope at 2.5 kV.

Results

Bacterial Inactivation after SC-$CO_2$ Treatment

Figure 2:
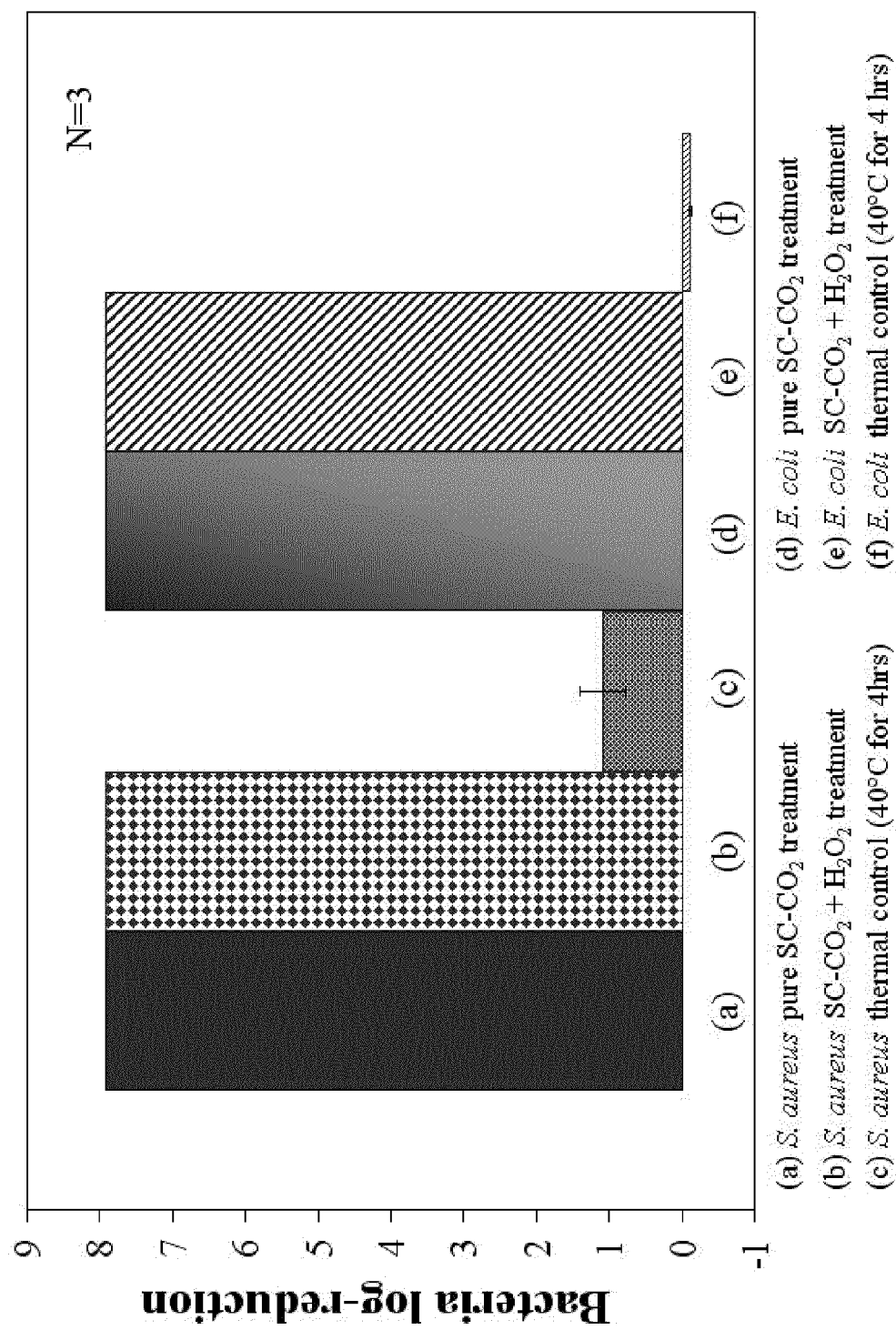
FIG. 2 shows a log-reduction of *S. aureus* and *E. coli* in the model hydrogel poly(acrylic acid-co-acrylamide) after pure $SC-CO_2$ and $SC-CO_2+H_2O_2$ treatments according to the examples (all treatment times were 4 hr at 40° C. and 27.6 MPa)

FIG. 2 shows inactivation (log-reduction) of *S. aureus-* and *E. coli*-inoculated hydrogels after treatment with pure $CO_2$ or $CO_2+H_2O_2$. A thermal control is also shown for which the inoculated gel was treated for 4 hours at 40° C., but with no applied $CO_2$. All treatments were for 4 hrs at 40° C. and 27.6 MPa. To quantify the bacteria on an inoculated gel, an untreated sample was pulverized (10 min, 230 rpm) and plated. Greater than 99% of the original bacteria count from culture was recovered. The suspension was optically clear and completely homogeneous after pulverization. Each sample was examined in triplicate.

Complete killing of *S. aureus* and *E. coli* was achieved after pure SC-$CO_2$ treatment at 27.6 MPa and 40° C. for 4 hours (FIGS. 2(*a*) and (*d*)). This is equivalent to an average of 7.72 and 7.93 log-reduction respectively. Therefore, pure $CO_2$ treatment is sufficient to achieve a high level of inactivation at the reported experimental conditions. As expected, after SC-$CO_2+H_2O_2$ treatments at the same experimental conditions (FIGS. 2(*b*) and (*e*)), complete bacteria kill was also achieved.

The average log-reduction of the thermal control was 1.09±10.31 for *S. aureus* (FIG. 2(*c*)) and (−0.12±10.01) for *E. coli* (FIG. 2(*f*)). *E. coli* grows well at a temperature range of 21 to 49° C. and the cell growth rate increases in response to increasing temperature (Farewell and Neidhardt 1998). This accounts for the small negative *E. coli* log-reduction. Bacterial inactivation is therefore due to $CO_2$ and not because of thermal inactivation.

Figure 3:
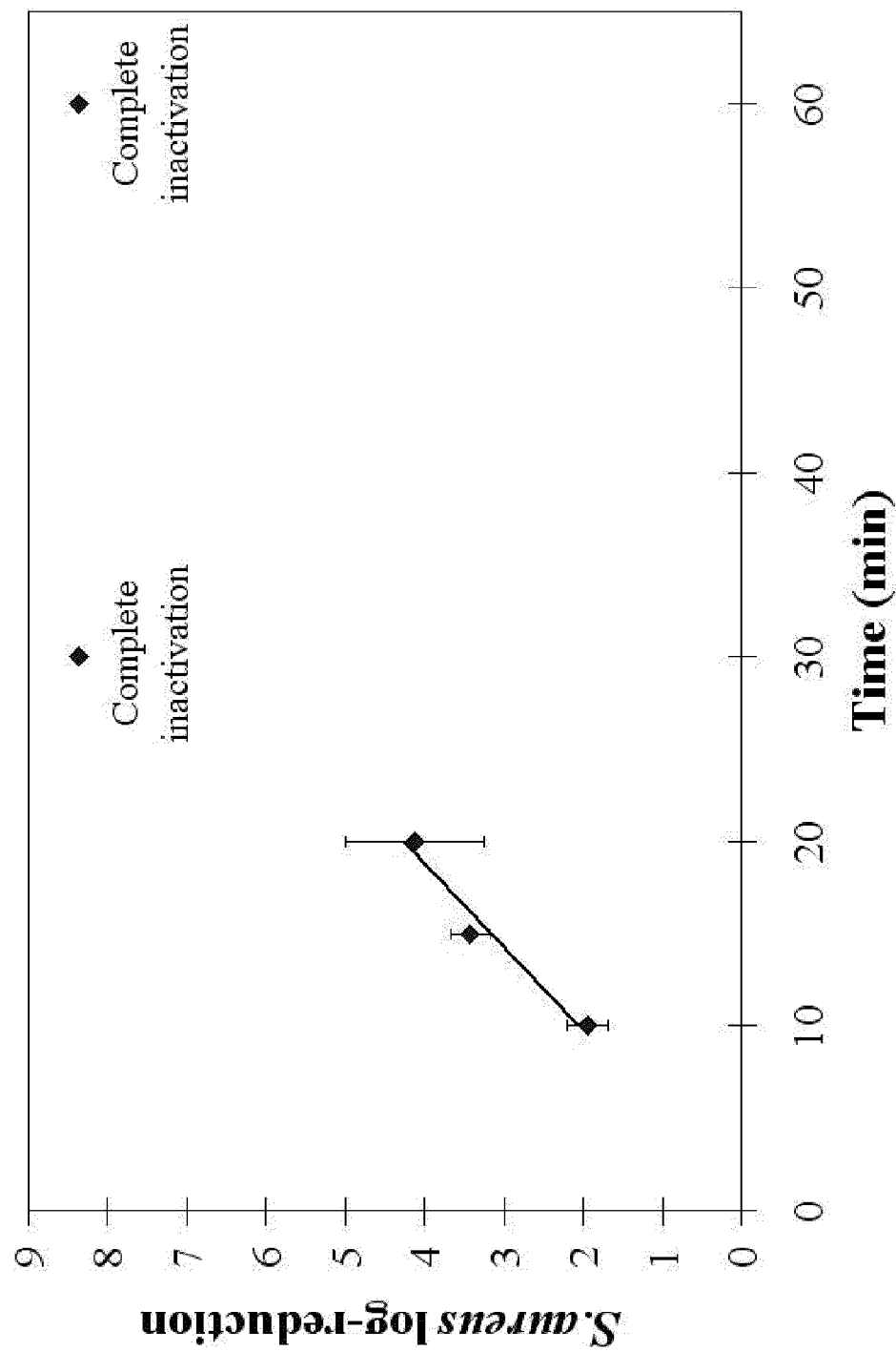
FIG. 3 shows log-reduction over time of *S. aureus* in the model hydrogel poly(acrylic acid-co-acrylamide) after pure $SC-CO_2$ treatment at 40° C. and 27.6 MPa ($D_{40}$=4.6) according to the examples.

The experiments of FIG. 2 were performed at longtimes (4 hrs of treatment) to follow previous experiments on bacterial spores (Zhang et al. 2006a). A subsequent set of experiments were performed at shorter treatment times because vegetative bacteria are less resistant to the sterilization process than spores. FIG. 3 shows the effect of processing time on the average log-reduction of *S. aureus* in the model hydrogel after pure SC-$CO_2$ treatment. At 40° C. and 27.6 MPa, the survival rate of *S. aureus* decreased roughly linearly with time until complete kill was achieved. After 60 and 30 minutes of treatment complete kill occurred. At times less than 30 minutes, incomplete kill is noted. At 40° C. and 27.6 MPa, a log-reduction of 4.13 is observed after 20 minutes of pure $CO_2$ processing. A 3.42 log-reduction was obtained after 15 minutes of treatment at the same experimental conditions A 1.94 log-reduction was observed after 10 minutes of $CO_2$ treatment.

It was not surprising that complete killing of *E. coli* after SC-$CO_2$ treatment might occur. Grain-positive and gram-negative bacteria have different responses to the gram stain, which originates from different peptidoglycan content. Gram-positive cell walls have a simple structure, but have thick peptidoglycan layers (10-20 layers thick, as much as 90% of the cell wall), which make the cell walls strong. On the other hand, gram-negative cells walls have complex structures but thinner peptidoglycan layers (only 1-2 layers thick, around 10% of the cell wall). Consequently, the gram-positive cells are more resistant and less permeable than grain-negative cells (Zhang et al. 2006c). *S. aureus* is a gram-positive bacteria and should be more resistant to $CO_2$ treatment than *E. coli*, which is gram-negative.

Difference in substrates may also contribute to differences in processing times. Previously, a $CO_2$ sterilization process was proven effective before for both *S. aureus* (Dillow et al. 1999; Kamihira et al. 1987) and *E. coli* (Ballestra et al. 1996; Debs-Louka et al. 1999; Dillow et al. 1999; Erkmen 2001a; Isenschmid et al. 1992; Kamihira et al. 1987; Schmidt et al. 2005) suspended in a liquid solution, in slurry form and when inoculated onto a solid hydrophilic medium but sterilization has not been investigated with the bacteria embedded in a polymeric matrix.

Physical Characterization of Hydrogel Samples

Hydrogels must be sterilized in a way that preserves their function. Standard sterilization methods have caused degradation in the structure and properties of tissue engineered scaffolds such as polyacrylamide gels (Lopatin et al. 2005). Thus, sterilization is not the only concern. The physical properties of the hydrogel after $CO_2$ processing are also very important. In order to investigate damage to the model hydrogel after treatment, a physical characterization investigation was performed.

Figure 4:
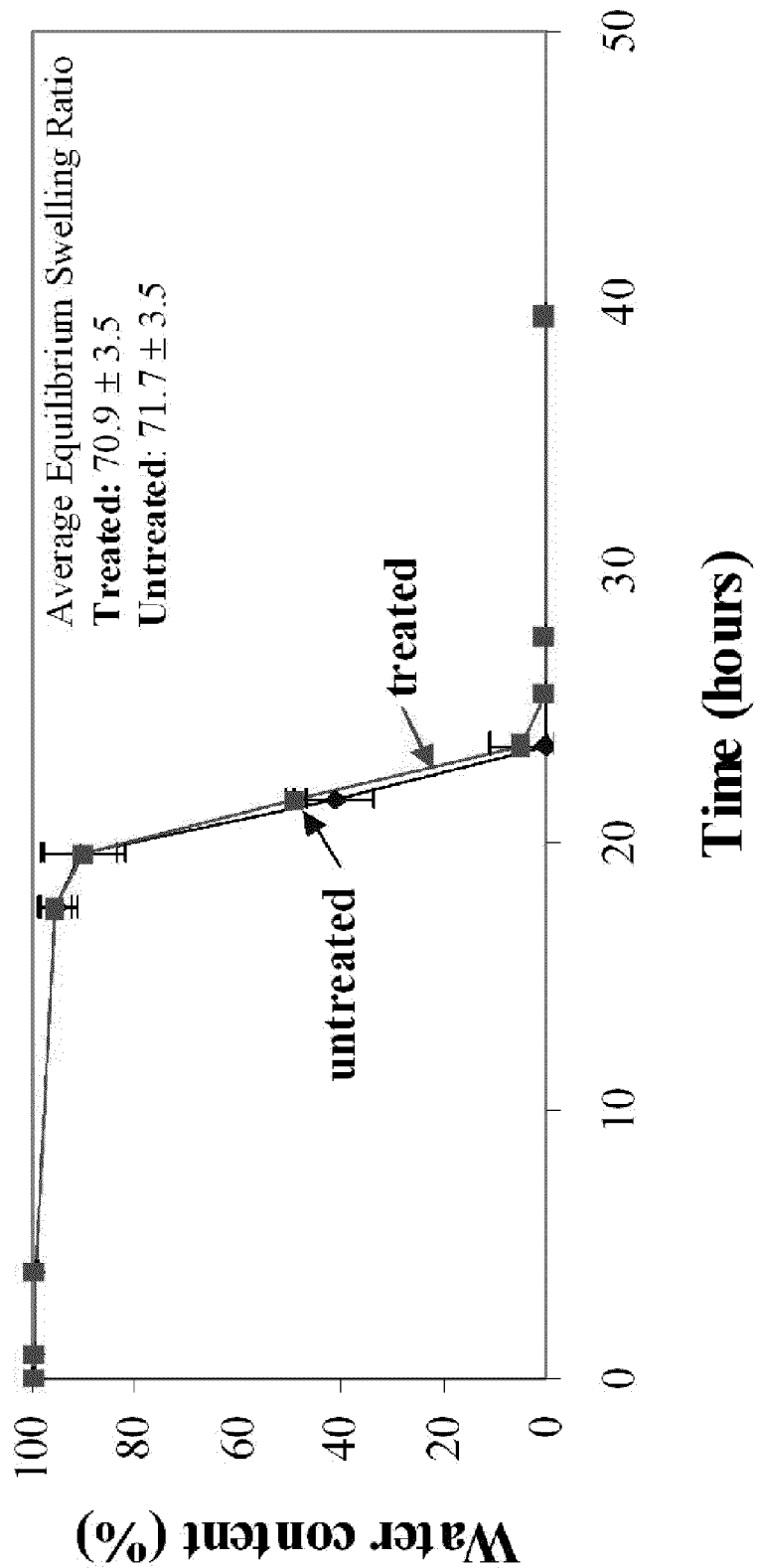
FIG. 4 shows a drying curve of poly(acrylic acid-co-acrylamide) potassium salt treated with $CO_2$ and $H_2O_2$ at 40° C. and 27.6 MPa for 4 hr, and hydrated with deionized water and dried in a vacuum oven at 50° C., 20 in Hg as an average of 3 different samples according to the examples.

To obtain drying curves, dry hydrogel particles were processed with SC-$CO_2$ plus 5 µL 30% $H_2O_2$ at 27.6 MPa and 40° C. for 4 hr prior. Subsequently the powders (and controls) were fully hydrated. Drying curves for hydrogels treated with $CO_2$+$H_2O_2$ are given in FIG. 4. The average equilibrium swelling ratio, a static property, was calculated before and after $CO_2$ processing. The average equilibrium swelling ratio was 70.9±3.5 for $CO_2$+$H_2O_2$ treated samples and 71.7±3.5 for untreated samples. Both treated and untreated samples absorbed almost equal quantity of water. FIG. 4 shows the dynamic properties of water removal. The drying curves for treated and untreated samples overlap, suggesting no change in hydrogel structure and therefore no apparent change in properties after $CO_2$ treatment. The water content remained near 100% for approximately 17 hours, and then suddenly decreased almost to 0% after 5 hours. This drying curve suggests that the water present in the sample was mostly bound water in a metastable state. After 17 hours of slow drying, a transition is reached at which the hydrogel network collapses fairly rapidly, and drying proceeds to completion. Neither static nor dynamic properties are affected by the $CO_2$ process as expressed by these drying curves.

Figure 5:
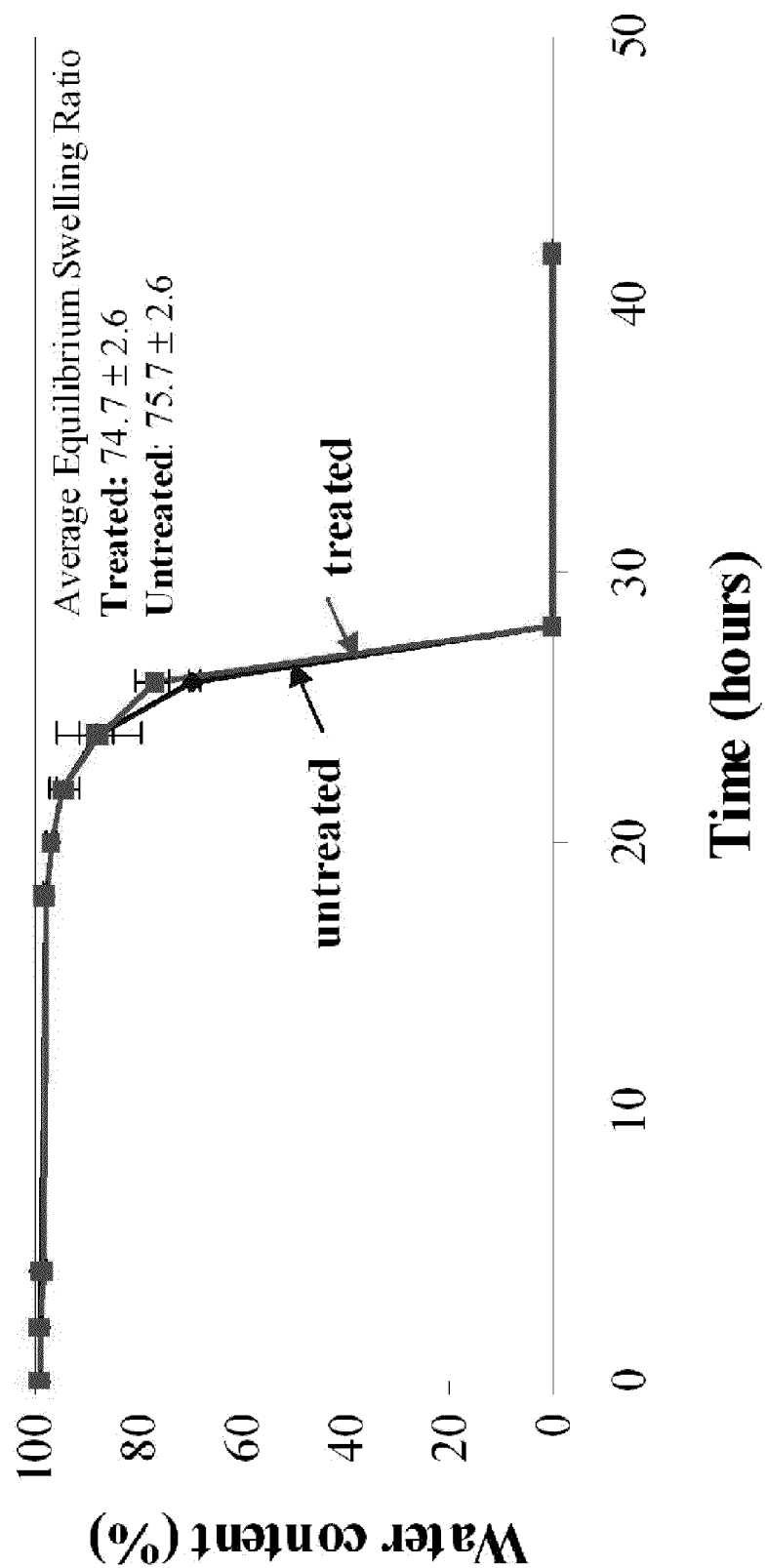
FIG. 5 shows a drying curve of crosslinked poly (acrylic acid-co-acrylamide) potassium salt treated with pure $CO_2$ at 40° C. and 27.6 MPa for 4 hr, hydrated with deionized water and dried in a vacuum oven (50° C., 20 inHg) as an average of 3 different samples according to the examples.

Drying curves for hydrogels treated with pure $CO_2$ are given in FIG. 5. The average equilibrium swelling ratio was 74.7±2.6 for the $CO_2$ processed samples and 75.7±2.6 for the untreated samples. Almost identical behavior is observed in FIGS. 4 and 5 (with the exception of a slower decrease in water content between approximately 17 and 27 hours), suggesting negligible effect of $H_2O_2$.

Figure 6:
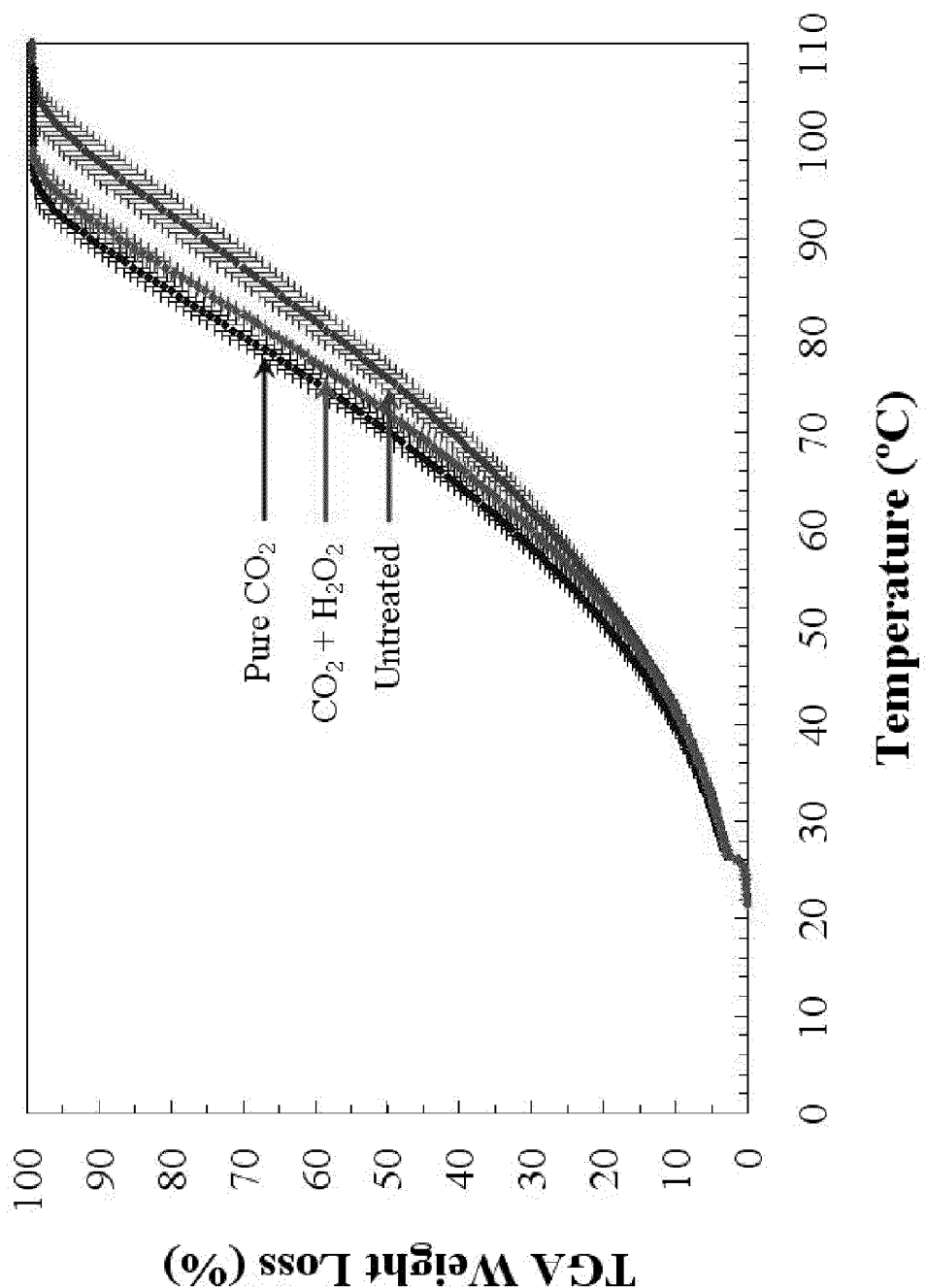
FIG. 6 shows TGA thermograms of hydrated crosslinked poly (acrylic acid-coacrylamide) potassium salt treated at 40° C. and 27.6 MPa for 4 hr according to the examples.

TGA results are shown in FIG. 6. Quantitative data presented in these curves are the results of three replicate measurements. The results are presented as mean □ standard deviation. Unlike the drying curves in FIG. 5, TGA analysis shows a noticeable difference between weight loss curves above 50° C. No significant difference between TGA curves is observed below 50° C. (i.e. the temperature at which the drying curves of FIGS. 4 and 5 were obtained). Thus, TGA suggests that the $CO_2$ process may cause slight changes in hydrogel properties that are manifested in the thermogram above 51° C. Treated samples lose water more rapidly than untreated samples at high temperatures. The percentages of free water and bound water appear to be different. Drying curves for gels treated with pure $CO_2$ and $CO_2$+$H_2O_2$ are very similar, indicating that addition of $H_2O_2$ does not cause noticeable oxidation of this model hydrogel. As shown by drying curves and TGA results, addition of $H_2O_2$ does not significantly affect the swelling characteristics of the model hydrogel. Differences between the drying curves and TGA results may be due to the amount of hydrogel used in the analysis. The large amount of hydrogel used for the drying curves (20 g) versus 10 to 20 mg used for TGA analysis made the drying curves more accurate.

Figure 7:
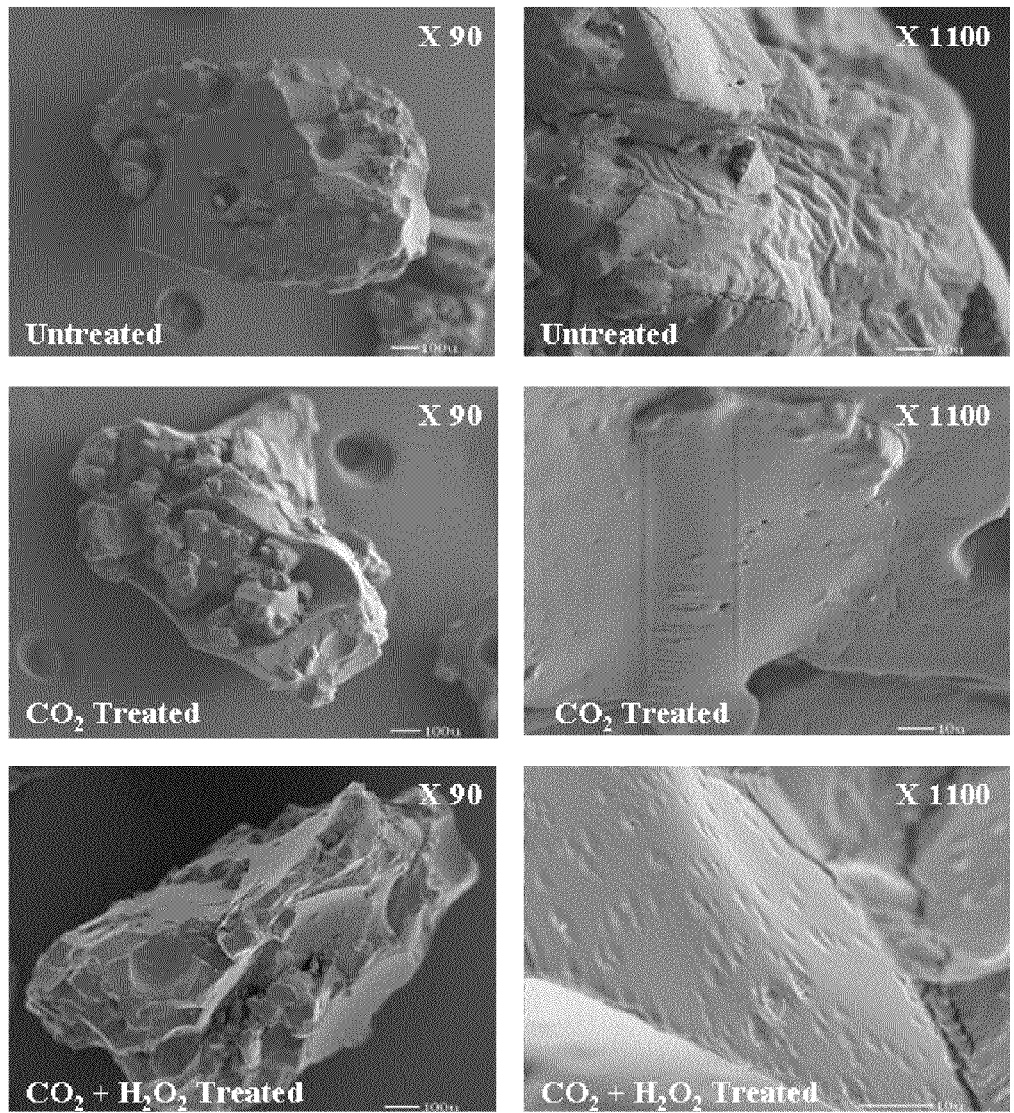
FIG. 7 shows SEM photographs of the surface structure of poly (acrylic acid-coacrylamide) potassium salt hydrogel untreated, $CO_2$ treated, and $CO_2$ plus 30% $H_2O_2$ treated according to the examples.

The surface morphology of the unswollen hydrogel is shown in FIG. 7. As observed in the figure, these specific gels have a heterogeneous amorphous structure that makes changes in structure difficult to visualize. Microporosity is not evident. No apparent micro structural changes are observed after processing with $CO_2$ or $CO_2$+$H_2O_2$. Morphological changes would be very important because many structural factors (e.g. charge, concentration of the ionizable groups, crosslink density and hydrophilicity) influence the degree of swelling of ionic polymers (Lee et al. 1999; Wu et al. 2001). As expected, no swelling changes were observed.

CONCLUSIONS

The work described herein establishes the effectiveness of $CO_2$-based technology in killing *S. aureus* and *E. coli* embedded in poly acrylic acid co-acrylamide potassium salt hydrogel. After pure SC-$CO_2$ treatment at 27.6 MPa and 40° C. for 4 hours, complete kill of *S. aureus* and *E. coli* was achieved. This is equivalent to an average of 7.72 and 7.93 log reduction respectively. Therefore, pure $CO_2$ treatment is sufficient to achieve a high level of inactivation at the reported experimental conditions. As expected, after SC$CO_2$ plus $H_2O_2$ treatments at the same experimental conditions, complete bacteria kill was also achieved. Bacteria inactivation occurs due to $CO_2$ and not because of thermal inactivation.

The survival rate of *S. aureus* in the model hydrogel after SC-$CO_2$ treatment at 40° C. and 27.6 MPa increased roughly linearly with time until complete kill was achieved. After 60 and 30 minutes of treatment complete eradication occurred. At times less than 30 minutes, incomplete kill is noted. The observed *S. aureus* log-reductions were 4.13, 3.42, and 1.94 after 20, 15, and 10 minutes respectively. *S. aureus* resistance to SC-$CO_2$ treatment was calculated with a D-value test. The D-value of $D_{40}$=4.6 minutes showed that about 27.4 minutes are required at the same experimental conditions (40° C. and 27.6 MPa) to obtain 6-log reduction of *S. aureus* in the model hydrogel.

Changes in the hydrogel structure due to $CO_2$ processing with pure $CO_2$ or $CO_2$ plus $H_2O_2$ were also evaluated. No significant changes were observed in the drying curves between treated (pure $CO_2$ or $CO_2$ plus 30% $H_2O_2$) and untreated samples. Average equilibrium swelling ratios for treated and untreated samples were also very similar. Therefore there is no observable change in the hydrogel properties after treatment. A significant difference between TGA weight loss curves of untreated, $CO_2$-treated and $CO_2$+$H_2O_2$-treated samples is observed at high temperatures. Differences between the drying curves and TGA results may be due to the amount of hydrogel analyzed. Addition of $H_2O_2$ does not significantly affect the swelling characteristics of the model hydrogel. Finally, microporosity is not distinguishable in SEM photographs of the hydrogel dry powder after treatment (pure $CO_2$ or $CO_2$ plus 30% $H_2O_2$). No changes in hydrogel dry powder structure are evident after treatment with either $CO_2$ or $CO_2$ plus 30% $H_2O_2$.

The novel $CO_2$ process completely sterilizes both bacteria on the model hydrogel. The physical properties were largely unaffected by exposure to $CO_2$ which suggests promise to employ this process for environment-sensitive gels. Successful development of this technology would remove a major barrier to commercialization of implantable biopolymers, especially those being developed for cell-based tissue engineering.

What is claimed:

1. A method of sterilizing a biocompatible hydrogel polymer, the method comprising:
treating the biocompatible hydrogel polymer with a supercritical $CO_2$ treatment composition at a treatment pressure and a treatment temperature, wherein the treatment pressure is about 4 MPa to about 30 MPa, and wherein the treatment temperature is about 5° C. to about 75° C.

2. The method as in claim 1, wherein the supercritical $CO_2$ treatment composition consists essentially of substantially pure $CO_2$.

3. The method as in claim 1, wherein the wherein the supercritical $CO_2$ treatment composition further comprises hydrogen peroxide.

4. The method as in claim 3, wherein hydrogen peroxide is present in the supercritical $CO_2$ treatment composition in an amount of about 10 ppm to about 1,000 ppm.

5. The method as in claim 3, wherein hydrogen peroxide is present in the supercritical $CO_2$ treatment composition in an amount of about 50 ppm to about 500 ppm.

6. The method as in claim 1, wherein the biocompatible hydrogel polymer comprises a poly(acrylic acid-co-acrylamide) hydrogel.

7. The method as in claim 1, wherein the biocompatible hydrogel polymer comprises a hydrogel based on poly(vinyl alcohol).

8. The method as in claim 1, wherein the biocompatible hydrogel polymer comprises a hydrogel based on methyl cellulose.

9. The method as in claim 1, wherein the biocompatible hydrogel polymer comprises a hydrogel based on hyaluronan or its derivatives.

10. The method as in claim 1, wherein the biocompatible hydrogel polymer comprises a silicon hydrogel.

11. The method as in claim 1, wherein the biocompatible hydrogel polymer is treated with the supercritical $CO_2$ treatment composition for about 30 minutes to about 5 hours.

12. The method as in claim 1, wherein treating the biocompatible hydrogel polymer kills about 90% or more of any *S. aureus* and *E. coli* present in the biocompatible hydrogel polymer.

13. The method as in claim 1, wherein treating the biocompatible hydrogel polymer kills about 95% or more of any *S. aureus* and *E. coli* present in the biocompatible hydrogel polymer.

14. The method as in claim 1, wherein treating the biocompatible hydrogel polymer kills about 99% to 100% of any *S. aureus* and *E. coli* present in the biocompatible hydrogel polymer.

* * * * *